(12) United States Patent
Anderson-Baron (10) Patent No.: US 11,991,994 B2
(45) Date of Patent: May 28, 2024

(54) METHOD FOR PRODUCING RECOMBINANT PROTEINS IN INSECTS

(71) Applicant: Future Fields Cellular Agriculture and Research LTD., Edmonton (CA)

(72) Inventor: Matthew Anderson-Baron, Edmonton (CA)

(73) Assignee: Future Fields Cellular Agriculture and Research LTD., Edmonton (CA)

( * ) Notice: Subject to any disclaimer, the term of this patent is extended or adjusted under 35 U.S.C. 154(b) by 470 days.

(21) Appl. No.: 17/086,226

(22) Filed: Oct. 30, 2020

(65) Prior Publication Data

US 2021/0127650 A1     May 6, 2021

Related U.S. Application Data

(60) Provisional application No. 62/927,788, filed on Oct. 30, 2019.

(51) Int. Cl.
*A01K 67/033*     (2006.01)

(52) U.S. Cl.
CPC ...... *A01K 67/0339* (2013.01); *A01K 2207/35* (2013.01); *A01K 2227/706* (2013.01); *A01K 2267/01* (2013.01); *A01K 2267/0393* (2013.01)

(58) Field of Classification Search
CPC ............ A01K 67/0339; A01K 2207/35; A01K 2227/706; A01K 2267/01; A01K 2267/0393
USPC ...................................................... 800/13, 4
See application file for complete search history.

(56) References Cited

U.S. PATENT DOCUMENTS

| | | |
|---|---|---|
| 6,361,966 B1 | 3/2002 | Walker et al. |
| 7,132,586 B2 | 11/2006 | Craig et al. |
| 9,279,000 B2 | 3/2016 | Sun et al. |

FOREIGN PATENT DOCUMENTS

| | | |
|---|---|---|
| WO | 2006023831 A3 | 3/2006 |
| WO | 2006132963 A2 | 12/2006 |
| WO | 2014099700 A1 | 6/2014 |

OTHER PUBLICATIONS

Beech et al. (2012) Collection of Biosafety Reviews, vol. 6, 66-124.*
Caldwell et al. (2012) Methods., vol. 56(1), doi:10.1016/j.ymeth.2011.12.002., pp. 1-18.*
Akmammedov et al. (Jul. 31, 2017) Scientific Reports, vol. 7:6899. DOI:10.1038/s41598-017-07282-w, p. 1-12.*
Kanca et al. (2017) Genetics, doi:https://doi.org/10.1534/genetics.117.199968, pp. 1-24.*
Marumoto et al. (1992) Biosci., Biotech., & Biochem., vol. 56(1), 13-16.*
Uhlirova et al. (2002) Develop. Genes and Evol., vol. 212:145-151.*
Aboalola et al. (2017) Stem Cells Int., vol. 2017, Article ID 8286248, 1-15.*
International Search Report received in PCT/US20/58418 dated Feb. 3, 2021.

\* cited by examiner

*Primary Examiner* — Anne Marie S Wehbe
(74) *Attorney, Agent, or Firm* — Run8 Patent Group, LLC; Peter Miller; Leah Raddatz (57) ABSTRACT

One variation of a method for producing a target compound includes: during an initial period, genetically modifying a population of insects to produce a target compound; during a growth period succeeding the initial period, cultivating the population of insects; during a treatment period succeeding the growth period, applying a dosage of a stressor to the population of insects, the stressor configured to trigger production of the target compound; in response to a proportion of the target compound within the population of insects exceeding a threshold proportion, harvesting the population of insects; homogenizing the population of insects to form a blend comprising the proportion of the target compound and a second proportion of a set of secondary components; and separating the proportion of the target compound from the second proportion of the set of secondary components for extraction of the proportion of the target compound from the blend.

16 Claims, 4 Drawing Sheets

METHOD FOR PRODUCING RECOMBINANT PROTEINS IN INSECTS

CROSS-REFERENCE TO RELATED APPLICATIONS

This Application claims the benefit of U.S. Provisional Application No. 62/927,788, filed on 30 Oct. 2019, which is incorporated in its entirety by this reference.

TECHNICAL FIELD

This invention relates generally to the field of cellular agriculture and more specifically to a new and useful method for producing recombinant proteins in the field of cellular agriculture.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

As shown in FIGS. 1-4, a method S100 for producing a target compound 120 includes: during an initial period, genetically modifying a population of insects 100 to produce a first target compound 120 in Block S102; during a growth period succeeding the initial period, cultivating the population of insects 100 according to a set of growth conditions in Block S110; and, during a treatment period succeeding the growth period, applying a first dosage of a first stressor to the population of insects 100, the first stressor configured to trigger production of the target compound 120 by the population of insects 100 in Block S120. The method S100 further includes, in response to a proportion of the first target compound 120 within the population of insects 100 exceeding a threshold proportion: harvesting the population of insects 100 in Block S130; homogenizing the population of insects 100 to form a blend including the proportion of the first target compound 120 and a proportion of a set of secondary components in Block S140; and separating the proportion of the first target compound 120 from the second proportion of the set of secondary components for extraction of the proportion of the target compound 120 from the blend in Block S150.

In one variation, genetically modifying the population of insects 100 to produce the first target compound 120 includes genetically modifying a genome of the population of insects 100 to include: a target sequence 112 encoding for the target compound 120; and a promoter sequence 114 coupled to the target sequence 112 and associated with the first stressor.

In one variation, the method S100 includes: during a growth period, cultivating a population of insects 100, from a first insect stage to a second insect stage, under a set of growth conditions in Block S110, the population of insects 100 genetically modified to produce a first target compound 120; and, during a treatment period succeeding the growth period, applying a first dosage of a first stressor to the population of insects 100, the first stressor configured to trigger production of the first target compound 120 by the population of insects 100 in Block S120. In this variation, the method S100 further includes, in response to a proportion of the first target compound 120 within the population of insects 100 exceeding a threshold proportion: harvesting the population of insects 100 in Block S130; homogenizing the population of insects 100 to form a blend including the proportion of the first target compound 120 and a proportion of a set of secondary components in Block S140; and separating the proportion of the first target compound 120 from the second proportion of the set of secondary components for extraction of the proportion of the target compound 120 from the blend in Block S150.

In another variation, the method S100 includes: during an initial period, genetically modifying a population of insects 100 to produce a first target compound 120 in Block S102; during a growth period succeeding the initial period, cultivating the population of insects 100 for a first duration under a first set of growth conditions in Block S110. The method S100 further includes, during a treatment period succeeding the growth period: applying a first dosage of a first stressor to the population of insects 100 to trigger production of the first target compound 120 at a first rate over a first treatment cycle in Block S120; and applying a second dosage of the first stressor, greater than the first dosage, to the population of insects 100 to trigger production of the target compound 120 at a second rate, greater than the first rate, over a second treatment cycle succeeding the first treatment cycle in Block S124; and, in response to a proportion of the first target compound 120 exceeding a threshold proportion during the treatment period, harvesting the population of insects 100 in Block S130. The method S100 further includes, during a purification period succeeding the treatment period: homogenizing the population of insects 100 to form a blend including the proportion of the first target compound 120 in Block S140; and extracting the proportion of the first target compound 120 from the blend in Block S150.

2. Applications

Generally, as shown in FIGS. 1-4, Blocks of the method S100 can be executed: to cultivate a genetically-modified population of insects 100 configured to generate a recombinant protein (or "target compound" 120); to control generation of this target compound 120 within the population of insects 100 via application of a particular stressor (e.g., heat-shock, cold-shock, UV exposure, nutrient-deficiency); and to extract and purify the target compound 120 from the population of insects 100.

More specifically, a genome of a population of insects 100 (e.g., a population of *Drosophila*) can be genetically-modified to include: a target sequence 112 encoding for the target compound 120; a promoter sequence 114 coupled to the target compound 120 and associated with the particular stressor, such that application of the particular stressor to the population of insects 100 enables activation of the promoter sequence 114, thereby activating transcription of the downstream target sequence 114, leading to expression and therefore production of the target compound 120. Therefore, the method S100 can be executed to induce production of large quantities of the target compound 120 via the genetically-modified population of insects 100.

Further, application of the stressor can be leveraged to both: increase expression of the target sequence 112 via pairing of the target sequence 112 with the promoter sequence 114 associated with the stressor; and decrease expression of other genes present in the genome coupled with the promoter sequence 114. For example, a heat-shock promoter sequence 114 (or "HSP70 promoter sequence" 114) can be coupled with a target sequence 112 within the genome of the population of insects 100. When a heat-shock stressor is then applied to this population of insects 100, the heat-shock promoter sequence 114 is activated and promotes transcription of the downstream target sequence 112. However, other genes in the genome that do not include the heat-shock-promoter sequence 114 may exhibit severely inhibited transcription. In addition, when the heat-shock stressor is applied, global translation is substantially halted. However, a leader sequence 116, defining a 5' untranslated region (or "5'UTR") of heat-shock proteins, can enable translation of heat-shock proteins during application of the stressor, while global translation is halted. In this example, the 5'UTR leader sequence 116 of heat-shock promoter sequence 114 can be included between the heat-shock promoter sequence 114 and the downstream target sequence 112 to enable translation of both heat-shock proteins and the target compound 120. Therefore, in this example, the heat-shock promoter sequence 114 can cooperate with the downstream target sequence 112 to increase enrichment of the target compound 120 encoded by the target sequence 112 within the population of insects 100.

By subjecting insects to conditions configured to induce production of the target compound 120, the population of insects 100 can function as a bioreactor configured to produce large quantities of the target compound 120. Unlike traditional bacterial systems implemented for production of recombinant proteins, the method S100 can be implemented to generate biologically active recombinant proteins, as propagation of the target sequence 112 within the population of insects 100 enables post-translational modifications, such as glycosylation. Further, once the genetically-modified genome is introduced into the population of insects 100, the genome can be propagated through each succeeding generation, requiring minimal maintenance for continued propagation of the genome. Additionally, a size of the population can be scaled accordingly to increase or decrease a quantity of the target compound 120 output by the population of insects 100. Therefore, the target compound 120 can be generated by the population of insects 100 via a scalable, efficient (e.g., high enrichment of the target compound 120 within the population of insects), and relatively lower-cost process. In one implementation, the population of insects 100 is a population of *Drosophila* (or "small fruit flies").

In one implementation, target compounds 120 extracted from the genetically-modified population of insects 100 can be incorporated as growth factors for generation of a growth media configured for cultured meat production (i.e., edible meat produced via growth of stem cells in culture as opposed to harvested from a slaughtered animal) Traditional processes for developing culture media for cultured meat products include supplementing the culture media with fetal bovine serum (or "FBS") including a mixture of nutrients, growth factors, hormones, lipids, and other components that support cell growth in culture. However, FBS is harvested from fetuses of pregnant cows prior to slaughter, thus resulting in ethical concerns regarding the production of cultured meat products. In addition, costs associated with FBS are increasingly high, resulting in slower growth of the cultured meat market. Conversely, the method S100 can be implemented to genetically-modify a population of insects 100 to produce a set of growth factors which can be mixed with a basal media (e.g., including salts, sugars, amino acids, vitamins) to generate a cost-effective, ethical, serum-free growth media capable of supporting cell growth in culture.

Further, in another implementation, in addition to cultured meat products, the growth factors generated by and extracted from the population of insects 100 can be configured for generation of growth media for production of cultured dairy products (e.g., cultured milk, cultured cheese, cultured ice cream). In yet another implementation, these growth factors can be configured for generation of cultured leather products.

For example, the method S100 can be executed to produce a set of growth factors (i.e., a set of target compounds 120), such as FGF2, TGF®, IGF1, and/or transferrin. The growth factors produced can be mixed into a growth factor cocktail that supplements a particular basal media to develop a species-specific serum-free growth media. Additionally or alternatively, each growth factor in the set of growth factors can be included in a single "complete" serum-free growth media configured for culturing myoblast and myocyte cell lines. Additionally or alternatively, different combinations of these growth factors, in the set of growth factors, can be included in different batches of the serum-free growth media, enabling customization of serum-free growth media based on a particular product and/or research.

In other various implementations, the method S100 can be executed to efficiently (e.g., high throughput, low cost) produce large quantities of a set of recombinant proteins (i.e., a set of target compounds 120) for implementation in development of vaccines, diagnostics, cosmetics, and/or therapeutics. For example, recombinant proteins generated by the population of insects 100 can include Cholera toxin B and/or collagen.

3. Growth Factors and Growth Media Production

In one implementation, the target compound 120 can define a growth factor configured for production of a growth media 130 for growing myoblasts in culture. In this implementation, the growth factor (i.e., the target compound 120) can be collected from a population of insects 100 according to methods and techniques described below and then mixed into a basal media to produce the growth media 130. For example, a quantity of the growth factor can be mixed with a volume of a basal media including a quantity of salts, a quantity of sugars, a quantity of amino acids, and a volume of buffers to generate a volume of a growth media 130.

The genetically modified population of insects 100 can be configured to produce a set of growth factors, such as: basic fibroblast growth factor (or "FGF2"); transforming growth factor beta (or "TGF®"); insulin-like growth factor (or "IGF"); transferrin; platelet-derived growth factor (or "PDGF"); vascular endothelial growth factor (or "VEGF") angiopoietin; epidermal growth factor; colony-stimulating factors; tumor necrosis factor-alpha (or "TNFα"); etc. In one implementation, a singular genetically-modified population of insects 100 can be configured to produce multiple growth factors. Alternatively, in another implementation, the singular genetically-modified population of insects 100 can be configured to produce a particular growth factor. In this implementation, multiple populations of insects 100 can be propagated, each population of insects 100 genetically-modified to produce a particular growth factor, in a set of growth factors.

Once a growth factor is generated and extracted from a population of insects 100, a quantity of the growth factor can be included in a volume of the growth media 130 at a particular concentration according to a type of growth factor and/or a type of growth media 130. In one example, a volume of a growth media 130 including Basic Fibroblast Growth Factor (or "FGF2") can include a quantity of FGF2 at a concentration of 0.1 milligrams per Liter. In another example, a volume of growth media 130 including Transforming Growth Factor Beta (or "TGF®") can be configured to include a quantity of TGF® at a concentration of 0.002 milligrams per Liter. In another example, a volume of growth media 130 including Insulin-like Growth Factor (or "IGF") can include a quantity of IGF at a concentration of 19.4 milligrams per Liter. In yet another example, a volume of growth media 130 including transferrin can include a quantity of transferrin at a concentration of 10.4 milligrams per Liter.

4. *Drosophila*

In one implementation, the population of insects 100 is a population of *Drosophila* genetically modified to produce a target compound 120.

As described above, "*Drosophila*" is referred to herein as a genus of flies belonging to the family Drosophilidae, members of which may be referred to as "small fruit flies," "pomace flies," "vinegar flies," and/or "wine flies." A population of *Drosophila* can include flies of a particular species, such as *D. melanogaster*(or "the common fruit fly"), *D. immigrans, D. innubila, D. funebris, D. neotestacea, D. virilise, D. hydei*, etc. For example, a population of *D. melanogaster* can be cultivated and configured for production of recombinant proteins. For example, the population of insects can include a population of *Drosophila melanogaster.*

A genome of the population of *Drosophila* can be genetically-modified to include a target sequence 112 encoding for the target compound 120. Once the genome is genetically-modified and inserted into the population of *Drosophila* (e.g., as embryos), the population of *Drosophila* can grow, reproduce, and propagate the genome through each subsequent generation of the population. Further, during a growth period, the population of *Drosophila* can be fed a simple and inexpensive diet including cornmeal-based gelatinous foods. Therefore, the population of *Drosophila* including the genetically-modified genome can be relatively inexpensive to maintain. In addition, because *Drosophila* exhibit relatively short lifespans (e.g., less than 50 days), new generations can be rapidly produced, enabling frequent collection of the target compound 120 from the population of *Drosophila*. Therefore, a large quantity of the target compound 120 can be collected over a relatively short period of time.

Unlike cell-based systems, *Drosophila* include immune systems and therefore exhibit lower risk of contamination within the population of *Drosophila*. Further, unlike bacterial systems, *Drosophila* can implement post-translational modification to produce biologically active recombinant proteins (i.e., biologically active target compounds 120).

The genome of the population of *Drosophila* can be genetically-modified via P-elements, present in *Drosophila*, which are transposable elements that enable genes to move within the genome. These P-elements can cooperate with transposons to insert an exogenous gene inserted within a vector into the genome of the *Drosophila* population. These P-elements of *Drosophila* therefore enable insertion of an exogenous gene (i.e., the target sequence 112) and expression of a resulting protein (i.e., the target compound 120) encoded by the exogenous gene into the genome of the population of *Drosophila*.

5. Genetic Modification of Insects

Block S102 of the method S100 recites genetically modifying a population of insects 100 to produce the first target compound 120. A population of insects 100 can be genetically modified to produce a particular target compound 120 (e.g., a particular growth factor). In particular, insect cells can be genetically modified to include a target sequence 112 encoding for the target compound 120, such that when the target sequence 112 is expressed, the insect cells generate the target compound 120.

In one implementation, the population of insects 100 can define a genetically-modified line of insects including multiple generations. In this implementation, a first generation of insects can be: genetically modified to produce a target compound 120 and then propagated to produce additional generations of insects configured to produce the target compound 120. For example, a first generation can be genetically modified to produce a target compound 120. In particular, a target sequence 112 encoding for the target compound 120 can be inserted into a genome of the first generation of insects. Once this target sequence 112 is stably integrated into the genome, this first generation can be propagated in cages over a propagation period, during which adult female insects in the first generation may lay eggs. These eggs develop into embryos which eventually hatch, thereby introducing new genetically-modified insect larvae defining a second generation of insects. The genome of this second generation thereby includes the target sequence 112—inherited from the first generation—encoding for the target compound 120. The target compound 120 can then be produced and collected from the second generation via the methods and techniques described below. Further, once the insect larvae in the second generation mature into adult insects, adult female insects in the second generation lay eggs and continue propagation of this line of genetically-modified insects. Therefore, in this implementation, once the genome of the first generation of insects is genetically modified to include the target sequence 112, this genome can be propagated through the line of insects, over multiple generations, without further genetic modification.

5.1 Regulatory Sequences

The genome of the population of insects 100 can be genetically modified to include a set of regulatory sequences upstream the target sequence 112. These regulatory sequences can be leveraged to control expression of the target sequence 112 and therefore control production of the target compound 120 expressed by the target sequence 112.

In one implementation, the set of regulatory sequences can include a promoter sequence 114 coupled to the target sequence 112. The promoter sequence 114 can be associated with a particular stressor (e.g., heat-shock, cold-shock, nutrient-deprivation, dehydration, UV exposure), such that application of the particular stressor to the population of insects 10 activates expression of the promoter sequence 114. For example, the genome of the population of insects 100 can be genetically modified to include an HSP70 promoter sequence 114 upstream the target sequence 112, such that activation of the HSP70 promoter 114 leads to expression of the target sequence 112 and thereby generation of the target compound 120. The HSP70 promoter sequence 114 can activate in the presence of a heat-shock stressor in order to express heat-shock proteins which may protect cells from damage caused by the heat-shock stressor. More specifically, in response to a particular dosage of a heat-shock stressor, the HSP70 promoter sequence 114—bound by a set of transcription factors—can initiate transcription of sequences immediately downstream the HSP70 promoter sequence 114. Therefore, by coupling the target sequence 112 to the HSP70 promoter sequence 114 immediately upstream the target sequence 112, a heat-shock stressor can be implemented to control transcription of the target sequence 112.

Therefore, in the preceding example, a heat-shock stressor can be applied to the population of insects 100 to increase production of the target sequence 120. Thus, in this implementation, the genome of the population of insects 100 can be genetically modified to include: a target sequence 112 encoding for a particular target compound 120; and a promoter sequence 114 upstream the target sequence 112 and associated with a particular stressor. By coupling the target sequence 112 with a promoter sequence 114 upstream of the target sequence 112, expression of the promoter sequence 114 can be leveraged to control expression of the target sequence 112 and, therefore, to control generation of the target compound 120.

In one implementation, the set of regulatory sequences can include both the promoter sequence 114 and a leader sequence 116 upstream the target sequence 112. In this implementation, the leader sequence 116 can be configured to enable translation of the target sequence 112 during application of a particular stressor, while the promoter sequence 114 can be configured to enable transcription of the target sequence 112. In particular, the genome of the population of insects 100 can be genetically modified to include: a target sequence 112 encoding for a particular target compound 120; a leader sequence 116 upstream the target sequence 112; and a promoter sequence 114 upstream the leader sequence 116 and associated with a particular stressor. The leader sequence 116 can be configured to activate translation of the target sequence 112 during application of the particular stressor once transcribed thereby enabling production of the target compound 112.

For example, a genome of a population of Drosophila can be genetically modified to include: a target sequence 112 encoding for a particular target compound 120; a 5'UTR leader sequence 116 upstream the target sequence 112; and an HSP70 promoter sequence 114 upstream the leader sequence 116 and associated with a heat-shock stressor; During application of the heat-shock stressor to the population of Drosophila, transcription is highly repressed. However, transcription remains enabled for genes involved in the heat shock response, such as the HSP70 promoter sequence 114. Therefore, by including the HSP70 promoter sequence 114 in the genome of the population of Drosophila, transcription of the target sequence 112 can be enabled during application of the heat-shock stressor, while transcription of other genes in the genome are repressed.

Further, during application of the heat-shock stressor, translation of genes in the genome is also repressed. In this example, the 5'UTR leader sequence 116 downstream the HSP70 promoter sequence 114 is configured to enable translation at increased temperatures at which non-heat-shock mRNAs exhibit decreased translation. Therefore, by including the 5-UTR leader sequence 116, translation of the target sequence 112 can also be enabled during application of the heat-shock stressor. Thus, in this example, the HSP70 promoter sequence 114 and the 5'UTR leader sequence 116 cooperate to enable both transcription and translation of the target sequence 112 during application of the heat-shock stressor, while other genes in the genome exhibit repressed transcription and translation. The target compound 120 can therefore be produced by the population of Drosophila with increased enrichment (e.g., increased mass of the target compound per unit mass of Drosophila flies).

In another implementation, the set of regulatory sequences can include both the promoter sequence 114 and an upstream activating sequence (or "UAS") upstream the target sequence 112. In this implementation, the upstream activating sequence can be configured to activate transcription of the target sequence 112. For example, a genome of a population of Drosophila can be genetically modified to include: a target sequence 112 encoding for a particular target compound 120; an upstream activating sequence upstream the target sequence 112 and configured to bind with a transcription factor (e.g., Gal4 transcription factor) to activate transcription of the target sequence 112; and a HSP70 promoter sequence 114 upstream the target sequence 112 and associated with a heat-shock stressor. In this example, the genome can be genetically modified to include a particular sequence encoding for the transcription factor configured to bind with the activating sequence. Therefore, in this example, the upstream activating sequence and the transcription factor can cooperate to regulate transcription of the target sequence 112.

In another implementation, the genome of the population of insects 100 can be configured to include a test sequence 118 configured to confirm insertion of the target sequence 112 into the genome. For example, the genome can include a test sequence 118 corresponding to a "white+" gene in Drosophila which, when expressed, results in red-eyed Drosophila. The test sequence 118 can be coupled to the target sequence 112 and flanked by the P-Element insertion sites. Injection can occur in white-eyed Drosophila. Therefore, by coupling the test sequence 118 to the target sequence 112, insertion of the target sequence 112 and the associated regulatory sequences can be confirmed via visual confirmation of expression of the test sequence 118 (e.g., via visual confirmation of red-eyed Drosophila).

5.2 Multiple Target Sequences

In one variation, the population of insects 100 can be genetically modified to produce a set of target compounds 120. In particular, cells of the population of insects 100 can be genetically modified to include a set of target sequences 112 corresponding to the set of target compounds 120. Therefore, in this variation, each insect in the population of insects 100 can be configured to generate multiple target compounds 120.

In this variation, each target sequence 112, in the set of target sequences 112, can be coupled to a promoter sequence 114, in a set of promoter sequences 114. Further, each promoter sequence 114, in the set of promoter sequences 114, can be associated with a particular stressor, in a set of stressors (e.g., heat-shock, nutrient deficiency, UV exposure, dehydration). By coupling each target sequence 112, in the set of target sequences 112, to a distinct promoter sequence 114, in the set of promoter sequences 114, expression of each target sequence 112 can be controlled via application of the set of stressors associated with the set of promoter sequences 114.

For example, cells of a population of Drosophila can be genetically modified to include: a first target sequence 112 encoding for a first target compound 120 (e.g., FGF2); a first promoter sequence 114 linked to the first target sequence 112 and associated with a first stressor (e.g., heat-shock); a second target sequence 112 encoding for a second target compound 120 (e.g., IGF1); and a second promoter sequence 114 linked to the second target sequence 112 and associated with a second stressor (e.g., UV exposure). Once this genetically-modified population of *Drosophila* is grown to a particular stage (e.g., larvae, pupae, adult), the first and second stressor can be applied at particular dosages, such as at particular quantities and intervals, to control production of the first and second target compounds 120 within the population of *Drosophila*.

Therefore, in this variation, a single genome of a population of insects 100 can be configured to generate multiple target compounds 120, generation of each target compound 120 controlled via application of various stressors to the population of insects 100. Thus, an entire set of growth factors required for production of a particular growth media 130—such as TGF-β, FGF2, IGF1, and transferrin for production of a growth media 130 for maintenance of stem cells in culture—can be generated and extracted from a single population of insects 100.

5.3 Detectable Signal Linked to Target Compound Generation

In one variation, the population of insects 100 is genetically modified to generate a detectable signal (e.g., an optical signal) indicating production of the target compound 120 by the population (e.g., when stressed). In particular, cells of the population of insects 100 can be genetically modified to include a reporter sequence linked to the promoter sequence 114 and/or target sequence 112 such that expression of the reporter sequence is linked to expression of the target sequence 112 in the population. Thus, expression of the reporter sequence by insects in the population can be configured to generate a signal (fluorescence, bioluminescence, and/or pigmentation change) that is directly detectable (e.g., with optical sensors or the human eye) and interpretable as an amount of the target compound present in the insect population without necessitating harvesting and/or chemical testing of the insect population. More specifically, in this variation, the population of insects 100 are genetically modified to include a reporter sequence linked to the promoter sequence 114 and/or to target sequence 112 to enable direct tracking of composition of the target compound 120 within the insect population 100 before, during, and after exposure to a stressor—and prior to harvesting the insect population 100—based on expression of the reporter sequence (e.g., presence and/or magnitude of a signal generated by the reporter sequence) within the insect population 100.

For example, the genome of the population of insects 100 can be genetically modified to include: a target sequence 112 encoding for a particular target compound 120; a promoter sequence 114 coupled to the target sequence 112; and a reporter sequence coupled to the promoter sequence 114. The reporter sequence can be configured to encode for a fluorescent protein, such that when the reporter sequence is expressed, a detectable fluorescent signal is generated. Therefore, a user (e.g., a lab technician, a researcher) may monitor fluorescence of insects in the population of insects 100 to confirm production of the particular target compound 120.

Further, in this variation, the user may estimate or measure (e.g., via a spectrometer) a magnitude of the signal to estimate a concentration of the particular target compound 120 within the population of insects 100. In the preceding example, the user may record an intensity of fluorescence generated by the population of insects 100 via a handheld spectrometer. This intensity measurement can be leveraged to estimate a concentration of the particular target compound 120 within the population of insects 100, and the population of insects can be continuously exposed or re-exposed to the stressor until the intensity of fluorescence of the insect population reaches an intensity of fluorescence corresponding to a target concentration of the particular target compound 120.

Therefore, in this variation, by pairing the promoter sequence 114 with a reporter sequence configured to generate a detectable signal when expressed, production of the target compound 120 can be readily confirmed. Furthermore, in this variation, the population of insects 100 can be exposed to a stressor in order to produce the target compound and the secondary signal, tested for magnitude of the secondary signal, and re-exposed to the stressor in order to increase magnitude of the secondary signal—and thus production of the target compound—up to a target signal magnitude that corresponds to a target proportion of the target compound within the insect population.

In one variation in which the genome of the population of insects 100 is genetically-modified to include multiple unique target sequences 112 configured to generate multiple unique target compounds 120, the genome can be further genetically-modified to include multiple reporter sequences 119. In this variation, the genome of the population of insects 100 can be genetically modified to include: a set of target sequences 112 encoding for a set of target compounds 120; a set of promoter sequences 114, each promoter sequence 114 coupled to a particular target sequence 112, in the set of target sequences 112, and associated with a particular stressor, in a set of stressors; and a set of reporter sequences 119, each reporter sequence 119 coupled to a particular target sequence 112, in the set of target sequences 112, and configured to express in response to expression of the particular target sequence 112.

5.4 Plasmid Generation and Insertion

In one implementation, the population of insects 100 can be genetically modified via insertion of a plasmid 110 (e.g., a pUAST plasmid, a pCaSpeR plasmid)—including the target sequence 112 encoding for the target compound 120—into the genome of the population of insects 100. The plasmid 110 can also be configured to include a set of regulatory sequences, such as the promoter sequence 114 and/or the leader sequence 116. In particular, the target sequence 112 and these regulatory sequences can be cloned via restriction enzyme cloning into a plasmid 110 including a multiple cloning site (or "MCS"). The target sequence 112 corresponding to the target compound 120 can be amplified via Polymerase Chain Reaction (or "PCR") with the addition of restriction cut sites for a set (e.g., one or two) of the restriction enzymes added onto 5' and 3' amplification primers, thus enabling inserting of the target sequence 112 into the vector at the MCS.

The resulting plasmid 110 vector including the target sequence 112 (e.g., a recombinant protein-coding sequence) can then be transformed into chemically competent bacterial cells for propagation. In particular, the plasmid 110 vector can be transformed via ampicillin selection. Once the plasmid 110 vector is propagated in the bacterial culture, the plasmid 110 DNA can be extracted from the bacterial culture and purified. Successful insertion of the target sequence 112 into the plasmid 110 vector can be verified by sequencing upstream and downstream from the insertion site (i.e., the MCS).

Upon confirmation of insertion of the target sequence 112 into the plasmid 110 vector, the target sequence 112 can be inserted into the genome of the population of insects 100. Once the target sequence 112 is integrated into the insect genome, the population of insects 100 can be propagated for production of the target compound 120.

Figure 1:
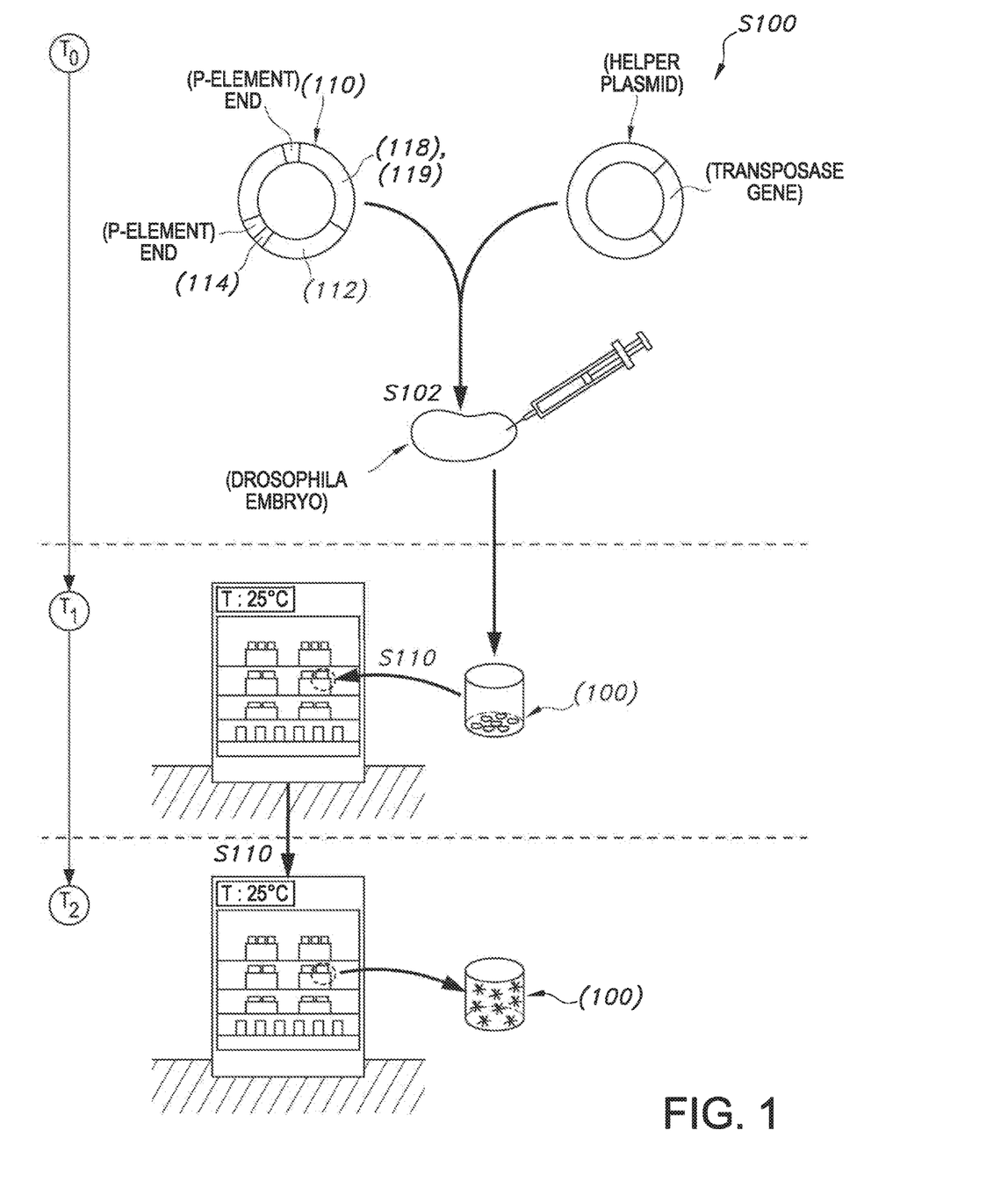
FIG. 1 is a flowchart representations of a method.
Figure 2:
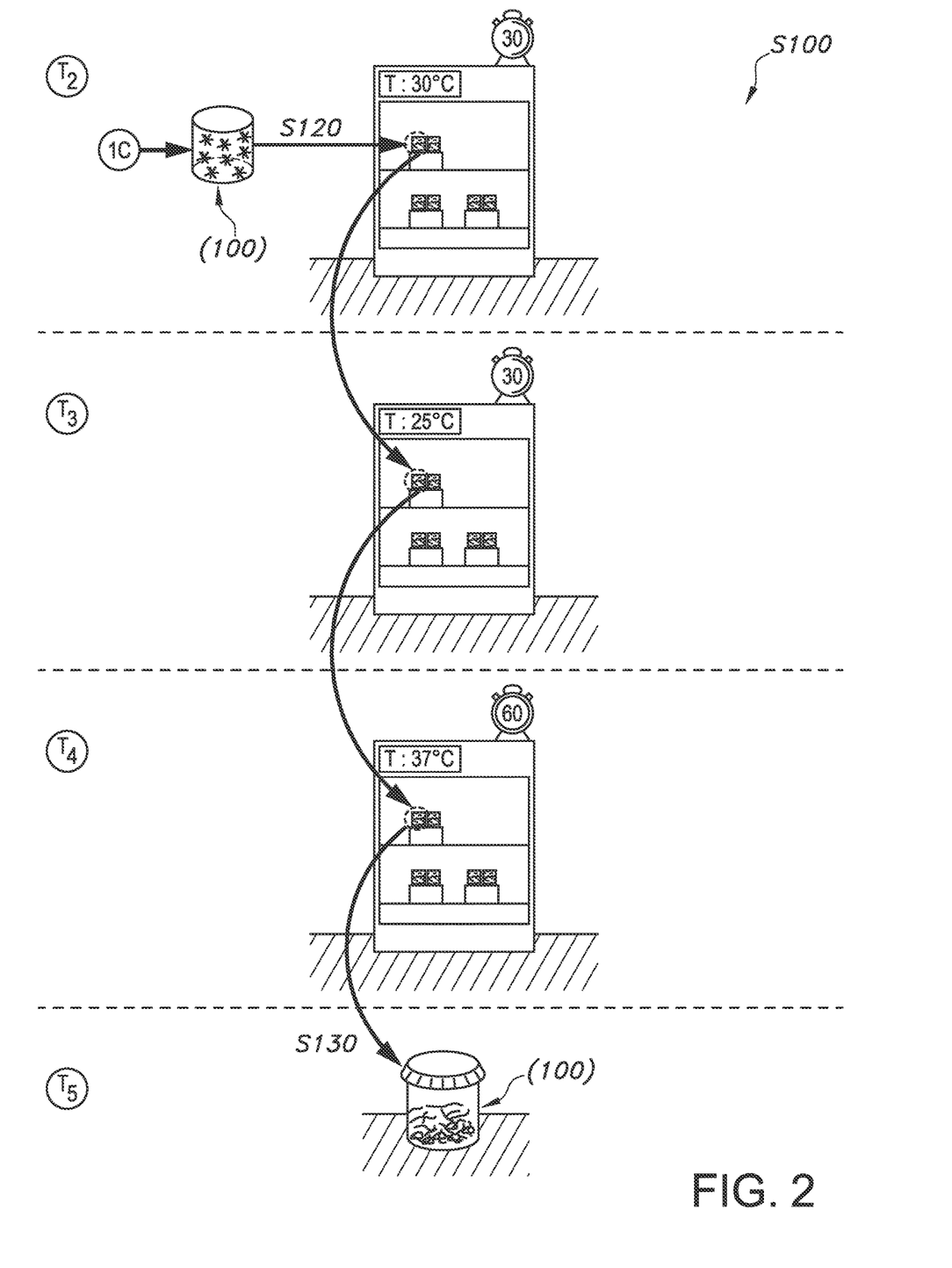
FIG. 2 is a flowchart representations of a method.
Figure 3:
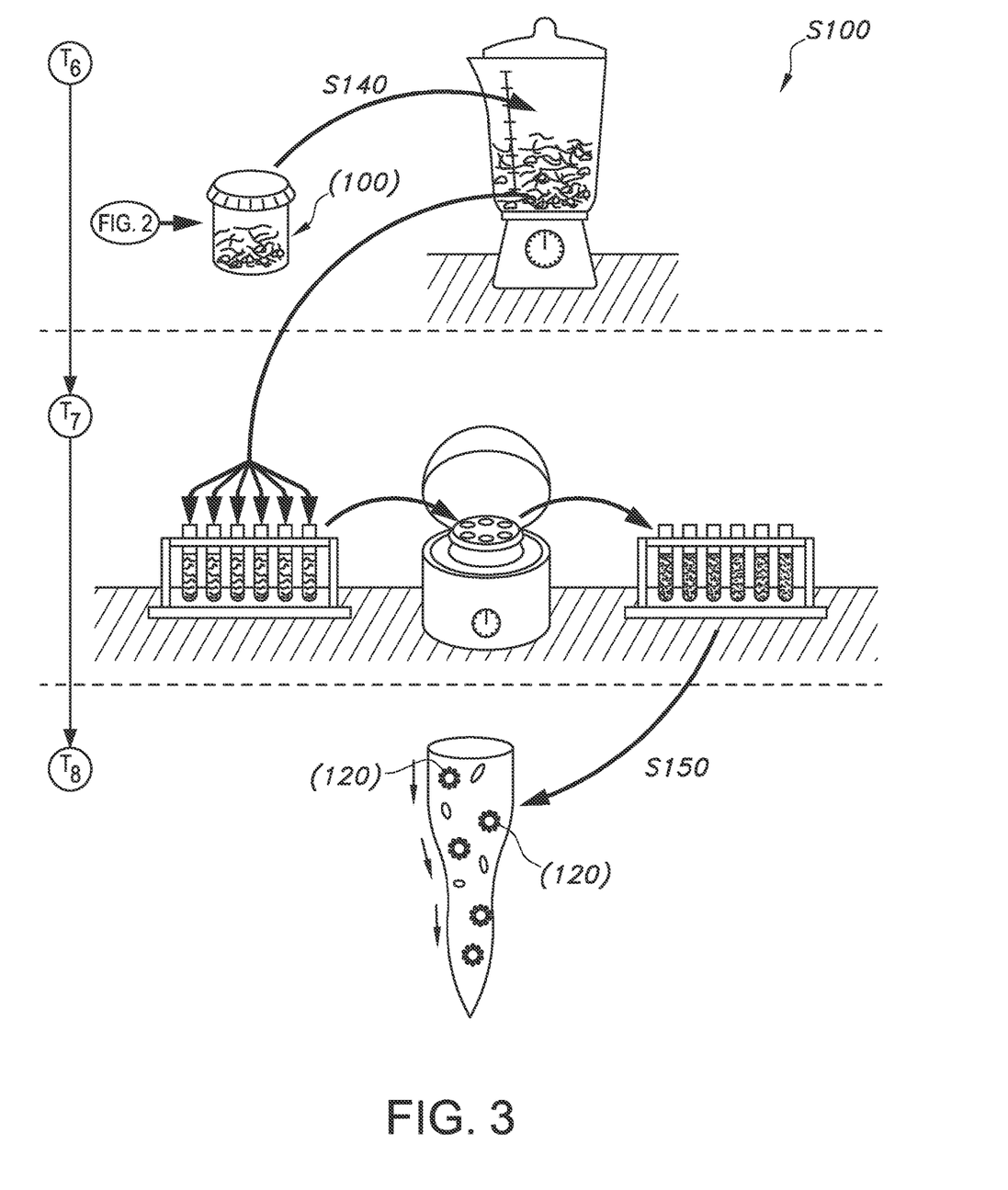
FIG. 3 is a flowchart representations of a method.
Figure 4:
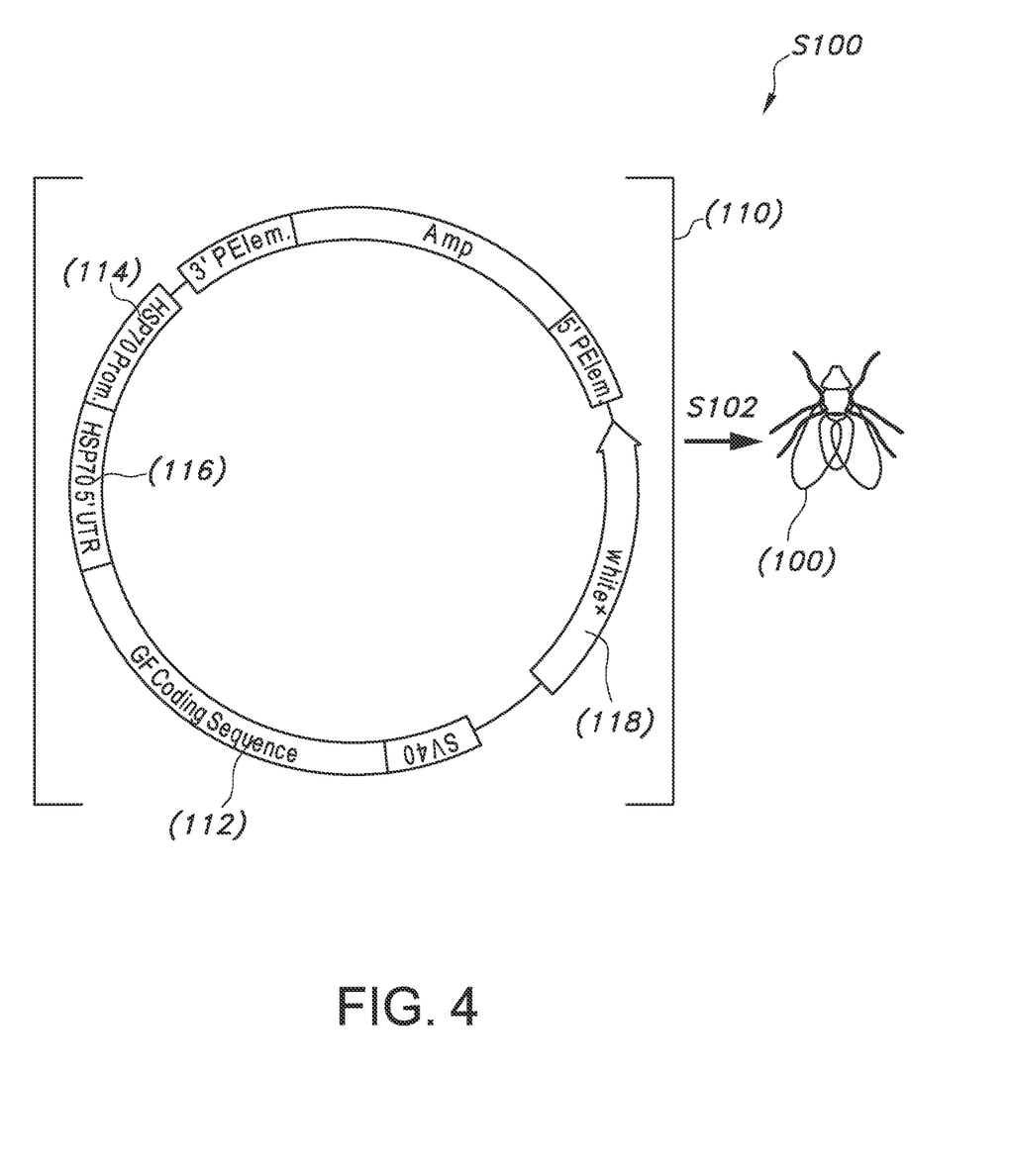
FIG. 4 is a schematic representation of genetic modification of *Drosophila*.

In one example, a population of Drosophila can be genetically modified to produce a target compound 120 via insertion of a recombinant pCaSpeR plasmid 110 into Drosophila embryos. In this example, as shown in FIG. 4, the plasmid 110 can be configured to include: a target sequence 112 encoding for a particular target compound 120; a set of regulatory sequences including a leader sequence 116 upstream the target sequence 112, and a promoter sequence 114 (e.g., an HSP70 promoter sequence) upstream of the leader sequence 116; and an ampicillin resistance gene configured to enable selection of transformants during propagation of the plasmid 110 in bacterial cells; a set of P-element sites configured for insertion of the plasmid 110 into Drosophila embryos; an MCS including a set of cut sites corresponding to a set of restriction enzymes (e.g., EcoRI, BgIII, NotI, XhoI, KpnI, and Xba1); and a test sequence 118 (e.g., corresponding to the white+ gene) configured to enable visual confirmation of propagation of the target sequence 112 in the population of Drosophila.

In this example, the target sequence 112 and regulatory sequences can be cloned via restriction enzyme cloning into the pCaSpeR plasmid 110. In particular, the target sequence 112 and regulatory sequences can be amplified via PCR with the addition of restriction cut sites for a subset (e.g., one or two) of restriction enzymes, in the set of restriction enzymes, added onto 5' and 3' amplification primers, thereby enabling insertion of the target sequence 112 into thepCaSpeR vector at the MCS via implementation of a T4 DNA ligase. Because the pCaSpeR vector includes the ampicillin resistance gene, the resulting pCaSpeR vector including the target sequence 112 can then be transformed into chemically competent bacterial cells for propagation via ampicillin selection. After propagation of the pCaSpeRvector in the bacterial culture, the plasmid 110 DNA can be extracted and purified. To confirm insertion of the target sequence 112 into the pCaSpeR vector, the plasmid 110 DNA can be sequenced upstream and downstream the MCS.

Once insertion of the target sequence 112 into the pCaSpeRT vector is confirmed, the target sequence 112 can be inserted into the Drosophila genome via P-element insertion. A P-element transposon present in the plasmid 110 vector at a P-element site, in the set of P-element sites, can be leveraged to integrate the exogenous target sequence 112 into the insect genome in the presence of a transposase. In particular, the target sequence 112 can be integrated into the Drosophila genome via germline transformation including microinjection of the plasmid 110 DNA and a helper plasmid 110 including transposase, into a recipient Drosophila embryo. Therefore, in this example, the plasmid 110 DNA can be physically delivered to a posterior pole of the syncytial blastoderm at which precursors of the germ cells form. Upon cellularization of the embryo, the plasmid 110 DNA—including the set of P-element sites—can be integrated into the genome of the germ cells via interactions between the transposase and P-elements at the set of P-element sites.

6. Growing the Population of Insects

Block S110 of the method S100 recites, during a growth period, cultivating the population of insects 100 according to a set of growth conditions. During the growth period, the population of insects 100 can be grown from a first stage (e.g., embryo) to a second stage (e.g., larvae, pupae, adult) over a duration of the growth period. During this growth period, the population of insects 100 can be subjected to a set of growth conditions (e.g., temperature, nutrient availability) configured to increase survival rates of insects in the population of insects 100 for the duration of the growth period.

For example, during the growth period, genetically-modified embryos of a population of Drosophila can be incubated at a set temperature of approximately (e.g., ±two degrees Celsius) twenty-five degrees Celsius. Once these embryos hatch to produce larvae, the population of Drosophila can be fed a particular diet (e.g., of cornmeal-based gelatinous foods). The population of Drosophila can be subjected to these conditions throughout the duration of the growth period, without introduction of a stressor.

In one implementation, the growth period can define a duration corresponding to transition to a particular life stage. For example, the population of Drosophila in the preceding example can be incubated at the set temperature over a first duration (e.g., 4 days) spanning a transition from embryo to a third instar larval stage. In this example, by terminating the growth period at the third instar larval stage, a concentration of the target compound 120 generated by the population of Drosophila can be quickly harvested before degradation of the target compound 120. Alternatively, in another example, the population of Drosophila can be incubated at the set temperature over a second duration (e.g., 5 days) spanning a transition from embryo, to larvae, to pupae. Alternatively, in yet another example, the population of Drosophila can be incubated at the set temperature over a third duration (e.g., 10 days, 15 days, 30 days) spanning a transition from embryo, to larvae, to pupae, to adult. In this example, the third duration can be selected to enable egg laying by female Drosophila prior to termination of the growth period for continued propagation of the target sequence 112 within the population of Drosophila.

7. Stressor Treatment

Block S120 of the method S100 recites, during a first treatment period succeeding the growth period, applying a first dosage of a first stressor to the population of insects 100, the first stressor configured to trigger production of the target compound 120 by the population of insects 100. After completion of the growth period, the population of insects 100 can be subjected to a stressor configured to control enrichment (e.g., unit mass of target compound 120 per unit mass of insects) of the target compound 120 within the population of insects 100. In particular, the first stressor can be configured to control enrichment of the target compound 120 via selective activation of the promoter sequence 114 associated with the first stressor and coupled to the target sequence 112.

For example, the genome of a population of Drosophila can be configured to include: a target sequence 112 encoding for a target compound 120; and a promoter sequence 114 associated with a heat-shock stressor and coupled to the target sequence 112. Then, during a first treatment period succeeding the growth period, the population of Drosophila can be subjected to a first dosage (e.g., an amount and duration) of the heat-shock stressor. In particular, in this example, the population of Drosophila can be shifted from incubation at the set of growth conditions (e.g., 25 degrees Celsius) to incubation at an increased temperature (e.g., between 35 degrees Celsius and 40 degrees Celsius). By subjecting the population of Drosophila to this heat-shock stressor, the promoter sequence 114 can be activated, thereby inducing expression of the target compound 120 encoded by the target sequence 112 coupled to the promoter sequence 114.

In one implementation, the treatment period can include a set of treatment cycles. In this implementation, the population of insects 100 can be subjected to multiple treatment cycles (e.g., 2 treatment cycles, 3 treatment cycles, 5 treatment cycles) during the treatment period in order to increase enrichment of the target compound 120 within the population of insects 100. For example, during a treatment period, a first dosage (e.g., a 12-degree temperature increase applied over 45 minutes) of a first stressor (e.g., heat-shock stressor) can be applied to the population of insects 100 over a first treatment cycle within the treatment period. Additionally, the first treatment cycle can also include a first rest period following application of the first dosage of the first stressor, during which the population of insects 100 can be returned to the set of growth conditions of the growth period. After this first rest period, a second dosage (e.g., approximating the first dosage, greater than the first dosage) can be applied to the population of insects 100 over a second treatment cycle within the treatment period. Similarly, the second treatment cycle can include a second rest period. Additionally, the treatment period can include a third treatment cycle, a fourth treatment cycle, and so on, in order to increase enrichment of the target compound 120. Therefore, the treatment period can include a particular quantity of treatment cycles configured to maximize enrichment of the target compound 120 within the population of insects 100.

7.1 Stressor Tolerance

In one implementation, the insect population can be exposed to stressor doses of increasing magnitude over successive treatment cycles in order to build tolerance to the stressor within the population of insects 100. In particular, a rate of production of the target compound 120 can be controlled via the dosage of the stressor applied to the population of insects 100. However, if the dosage of the stressor is increased too quickly, the population of insects 100 may not survive application of the stressor. Therefore, a lower dosage of the stressor can initially be applied during a first treatment cycle, followed by a higher dosage during a subsequent treatment cycle, thus increasing tolerance of the insects to the stressor and enabling application of increased dosages of the stressor for increased enrichment of the target compound 120 within the population of insects 100.

For example, on Day-20 of a lifespan of a population of *Drosophila*, a first dosage (e.g., a five-degree temperature increase applied over 15 minutes) of a first stressor (e.g., a heat-shock stressor) can be applied to the population of *Drosophila* over a first treatment cycle. During the first treatment cycle, the first dosage of the first stressor can be configured to trigger production of the target compound 120 at a first rate. Five days later, on Day-30 of the lifespan, a second dosage (e.g., an eight-degree temperature increase applied over 30 minutes) of the first stressor can be applied to the population of *Drosophila* over a second treatment cycle, the second dosage greater than the first dosage. During the second treatment cycle, the second dosage of the first stressor can be configured to trigger production of the target compound 120 at a second rate greater than the first rate. Finally, two days later, on Day-32 of the lifespan, a third dosage (e.g., a twelve-degree temperature increase applied over a 45-minute treatment interval) can be applied to the population of *Drosophila* over a third treatment cycle, the third dosage greater than the first and second dosage. Similarly, the third dosage of the first stressor can be configured to trigger production of the target compound 120 at a third rate greater than the first and second rate.

7.2 Multiple Stressors

In one variation, the population of insects 100 can be configured to produce multiple target compounds 120. In this variation, each target compound 120 can be linked to a particular stressor, in a set of stressors, such that production of each target compound 120 can be regulated via application of the set of stressors.

For example, the population of insects 100 can be genetically modified to include: a first target sequence 112 encoding for a first target compound 120; a first promoter sequence coupled to the first target sequence 112 and associated with a heat-shock stressor; a second target sequence 112 encoding for a second target compound 120; and a second promoter sequence coupled to the second target sequence 112 and associated with a cold-shock stressor. In this example, the population of insects 100 can be exposed to both the heat-shock stressor and the cold-shock stressor in controlled proportions to produce both the first and second target compounds 120 in controlled proportions. Therefore, a single population of insects 100 can be configured to produce two different target compounds 120, thereby increasing redundancy across multiple different insect populations 100 with different combinations of promoter sequences 114 and target sequences 112.

In this variation, each stressor, associated with a promoter sequence 112, can be applied to the population of insects 100 over multiple treatment cycles to increase enrichment of the target compounds 120 within the population of insects 100. In particular, in the preceding example, the population of insects 100 can be grown in a primary incubator set at 25 degrees Celsius during a growth period. After completion of the growth period, the population of insects 100 can be placed in an incubator at 30 degrees Celsius for a first duration of 10 minutes for a first cycle of the heat-shock stressor. Upon expiration of the first duration, the population of insects 100 can be placed back in the primary incubator at 25 degrees Celsius. After a first rest period (e.g., 15 minutes, 1 hour, 12 hours), the population of insects 100 can be placed in an incubator at 20 degrees Celsius for a second duration of 10 minutes for a first cycle of the cold-shock stressor. Upon expiration of the second duration, the population of insects 100 can again be placed in the primary incubator at 25 degrees Celsius. The first cycle of both the heat-shock and cold-shock stressors can be configured to increase tolerance of the population of insects 100 to these stressors before increasing magnitude of these stressors.

Later, after a second rest period (e.g., 15 minutes, 1 hour, 12 hours)—during which the population of insects 100 remain in the primary incubator at 25 degrees Celsius—the population of insects 100 can be moved into an incubator set at 37 degrees Celsius for a third duration of 45 minutes for a second cycle of the heat-shock stressor. Upon expiration of the second duration, the population of insects 100 can be placed in the primary incubator. After a third rest period, the population of insects 100 can be placed in an incubator at 15 degrees Celsius for a fourth duration of 45 minutes. Upon expiration of the fourth duration, the population of insects 100 can be placed in the primary incubator. A dosage (e.g., magnitude and duration) of both the first and second stressor can be increased and/or maintained over multiple treatment cycles to acclimate the population of insects 100 to these stressors and to increase enrichment of the first and second target compounds 120 within the population of insects 100.

8. Harvesting Insects

Block S130 of the method S100 recites, in response to a proportion of the first target compound 120 within the population of insects 100 exceeding a threshold proportion, harvesting the population of insects 100. After completion of the stressor treatment, the population of insects 100 can be harvested for collection of the target compound 120.

In one implementation, the population of insects 100 can be harvested once a particular quantity of the target compound 120 has been produced. For example, the population of insects 100 can be harvested in response to a quantity (e.g., proportion, concentration) of the target compound 120 within the population exceeding a threshold quantity (e.g., concentration of two percent, five percent, fifteen percent). In this example, the genome of the population of insects 100 can include the reporter sequence 119 configured to generate the detectable signal indicating generation of the target compound 120. Therefore, a magnitude of this detectable signal can be interpreted for estimating the quantity of the target compound 120 within the population of insects 100. Alternatively, other methods and techniques can be implemented to estimate concentration of the target compound 120.

In one implementation, the population of insects 100 can be harvested after a set quantity of treatment cycles configured to generate a concentration of the target compound 120 exceeding a threshold concentration. For example, for a particular target compound 120, for a first generation of the population of insects 100, a first quantity of treatment cycles can be applied. Upon extraction of the particular target compound 120 for this first generation, a first concentration of the particular target compound 20 (e.g., mass of the particular target compound 120 per mass of the first generation of insects) can be recorded. Later, for a second generation of the population of insects 100, a second quantity of treatment cycles can be applied. Upon extraction of the particular target compound 120 for this second generation, a second concentration of the particular target compound 20 can be recorded. Over time, this process can be repeated over numerous generations of the population of insects 100 to develop a model for the particular target compound 120 for maximizing concentration of the particular target compound 120 within the population of insects 100. Therefore, based on the model, a set quantity of treatment cycles—configured to yield maximum concentration of the particular target compound 120—can be identified.

Block S140 of the method S100 recites homogenizing the population of insects 100 to form a blend including the proportion of the first target compound 120 and a proportion of a set of secondary components. In one implementation, the population of insects 100 can be mechanically homogenized in a particular buffer matched to the target compound 120 to form a blend. For example, the euthanized population of insects 100 can be mixed in a blender with a particular buffer over a set duration to form a homogenous mixture (i.e. the blend) from which the target compound 120 can be readily extracted.

9. Protein Purification

Block S150 of the method S100 recites separating the proportion of the first target compound 120 from the second proportion of the set of secondary components for extraction of the proportion of the target compound 120 from the blend.

In one implementation, the target compound 120 can be extracted from the blend via affinity chromatography. In this implementation, the blend can be centrifuged to separate out any insoluble materials remaining from the insects, resulting in a supernatant (e.g., a homogenous mixture) including the proportion of the target compound 120 and the second proportion of the set of secondary components. This supernatant can be passed over a column including a stationary phase configured to capture the proportion of the target compound 120. For example, the stationary phase can include a particular type of beads (e.g., Sepharose beads) including antibodies or receptors configured to selectively bind to the target compound 120 to extract the proportion of the target compound 120 from the supernatant. In this implementation, the proportion of the secondary components of the supernatant can then be washed off of the column, such that only the proportion of the target compound 120 remains bound to the column. This proportion of the target compound 120 can then be eluted off of the beads of the column, such as by washing the column with a competitive ligand or a high salt solution configured to disrupt interactions between the target compound 120 and antibodies or receptors of the beads.

In another implementation, the target compound 120 can be extracted from the blend via size exclusion chromatography. In this implementation, the blend (e.g., a homogenous mixture) can similarly be centrifuged to separate out any solid materials, resulting in the supernatant (e.g., a homogenous mixture) including the proportion of the target compound 120 and the second proportion of the set of secondary components. The supernatant can then be run over a column including pores of a particular size range configured to trap biomolecules in the supernatant based on molecular size. For example, the column can be configured to include pores within the particular size range such that: smaller biomolecules in the supernatant become trapped in these pores and thus elute more slowly; and large biomolecule are blocked from entering these pores and thus elute more quickly. Therefore, retention times of the target compound 120 and each secondary component, in the set of secondary components, can be estimated based on molecular size. Thus, the target compound 120 can be separated and collected based on retention time within the column.

Additionally or alternatively, in another implementation, both affinity chromatography and size exclusion chromatography can be implemented in combination for extraction of the target compound 120 from the blend. For example, the supernatant can be run over a first column configured to purify the target compound 120 via size exclusion chromatography. Then, the supernatant can be run over a second column configured to further purify the target compound 120 via affinity chromatography. Alternatively, in yet another implementation, ion-exchange chromatography can be implemented for extraction of the target compound 120.

In another implementation, the target compound 120 can be extracted from the blend via three phase partitioning (or "TPP"). In this implementation, the proportion of the target compound 120 can be precipitated out of the supernatant via addition of t-butanol and ammonium sulfate. The t-butanol can bind to the proportion of the target compound 120 in the supernatant, enabling the proportion of the target compound 120 to float above the aqueous supernatant solution. The proportion of the target compound 120—floating above the aqueous solution—can then be extracted. This proportion of the target compound 120 can then be dissolved in a separate solution to regain functionality.

10. Other Target Proteins

As described above, the target compound 120 can define a growth factor configured for integration in a growth media. In one implementation, the target compound 120 can define a growth factor configured for integration in a growth media for culturing myoblast and myocyte cell lines. Alternatively, in another implementation, the target compound 120 can define a growth factor configured for integration in a growth media for cell culture in pharmaceutical and academic research applications.

In one variation, the target compound 120 can define a recombinant protein for integration in other applications such as: pharmaceuticals; therapeutics; vaccines; diagnostics; cosmetics; etc. For example, the target compound 120 can define a Cholera toxin B protein or a collagen protein.

The target compound 120 can be produced at different purities (or "grades") based on the final product of the target compound 120. For example, the target compound 120 can be produced in a solubilized concentrate form for integration in a growth media for culturing cells. Alternatively, in another example, the target compound 120 can be produced at a pharmaceutical grade for production of growth media for cell culture in pharmaceutical and academic research application. This target compound 120 can be produced at a higher purity in order to achieve the pharmaceutical grade. Therefore, in this example, the population of insects 100 can be treated and/or maintained under a particular set of conditions in order to minimize contamination and increase purity of the final target compound 120.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method comprising:
   during an initial period, genetically modifying a population of *Drosophila* to produce a first target compound, a genome of the population of *Drosophila* comprising:
   a first target sequence corresponding to the first target compound; and
   a first promoter sequence coupled to the first target sequence and activated by a first stressor comprising a heat stress;
   during a growth period succeeding the initial period, cultivating the population of *Drosophila* according to a set of growth conditions;
   during a treatment period succeeding the growth period, applying a first dosage of the first stressor to the population of *Drosophila* to trigger production of the target compound in the population of *Drosophila* via activation of the first promoter sequence;
   estimating a first concentration of the first target compound within the population of *Drosophila*;
   in response to the first concentration falling below the threshold concentration, applying a second dosage of the first stressor to the population of *Drosophila*; and
   in response to the first concentration of the first target compound exceeding the threshold concentration:
   harvesting the population of *Drosophila*;
   homogenizing the population of *Drosophila* to form a blend comprising the first concentration of the first target compound and a second concentration of a set of secondary components; and
   separating the first target compound from the set of secondary components for extraction of the target compound from the blend.

2. The method of claim 1:
   wherein cultivating the population of *Drosophila* during the growth period comprises cultivating the population of *Drosophila* during the growth period spanning a transition of the population of *Drosophila* from an embryonic stage to a larval stage; and
   wherein harvesting the population of *Drosophila* in response to the first concentration of the first target compound within the population of *Drosophila* exceeding the threshold concentration comprises harvesting the population of *Drosophila* in the larval stage in response to the first concentration of the first target compound within the population of *Drosophila* exceeding the threshold concentration.

3. The method of claim 1:
   wherein cultivating the population of *Drosophila* during the growth period comprises cultivating the population of *Drosophila* during the growth period spanning a transition of the population of *Drosophila* from an embryonic stage to an adult stage; and
   wherein harvesting the population of *Drosophila* in response to the first concentration of the first target compound within the population of *Drosophila* exceeding the threshold concentration comprises harvesting the population of *Drosophila* in the adult stage in response to the first concentration of the first target compound within the population of *Drosophila* exceeding the threshold concentration.

4. The method of claim 1, further comprising:
   during the initial period, genetically modifying the genome of the population of *Drosophila* to include a reporter sequence coupled to the promoter sequence and encoding for a reporter compound configured to generate a detectable signal; and
   during the treatment period:
   recording a magnitude of the detectable signal; and
   estimating the first concentration of the first target compound in the population of *Drosophila* based on the magnitude of the detectable signal.

5. The method of claim 4:
   wherein genetically modifying the population of *Drosophila* to include the reporter sequence comprises genetically modifying the genome of the population of *Drosophila* to include the reporter sequence encoding for a fluorescence reporter configured to produce a fluorescent signal within the population of *Drosophila*;
   wherein recording the magnitude of the detectable signal comprises recording an intensity of the fluorescent signal; and
   wherein estimating the first concentration of the first target compound based on the magnitude of the detectable signal comprises estimating the first concentration of the first target compound based on the intensity of the fluorescent signal.

6. The method of claim 1, wherein separating the first target compound from the set of secondary components for extraction of the target compound comprises separating the first target compound from the set of secondary components for extraction of the first target compound from the blend via affinity chromatography.

7. A method comprising:
during a growth period, cultivating a population of *Drosophila* according to a set of growth conditions, the population of *Drosophila* genetically modified to produce a first target compound and comprising:
a first target sequence corresponding to the first target compound; and
a first promoter sequence linked to the first target sequence and activated by a first stressor comprising a heat stress;
during a treatment period succeeding the growth period:
during a first treatment cycle, applying a first dosage of the first stressor to the population of *Drosophila*, the first stressor configured to trigger production of the first target compound in the population of *Drosophila* via activation of the first promoter sequence;
at a first time succeeding the first treatment cycle, estimating an initial concentration of the first target compound generated within the population of *Drosophila*; and
in response to the initial concentration falling below a threshold concentration, applying a second dosage of the first stressor to the population of *Drosophila* during a second treatment cycle; and
in response to a first concentration of the first target compound within the population of *Drosophila* exceeding the threshold concentration:
harvesting the population of *Drosophila*;
homogenizing the population of *Drosophila* to form a blend comprising the first concentration of the first target compound and a second concentration of a set of secondary components; and
separating the first concentration of the first target compound from the second concentration of the set of secondary components for extraction of the first target compound from the blend.

8. The method of claim 7:
wherein cultivating the population of *Drosophila* according to the set of growth conditions during the growth period comprises incubating a population of *Drosophila*, within a first temperature range, during the growth period spanning a transition of the population of *Drosophila* from an embryonic stage into an adult stage;
wherein applying the first dosage of the first stressor to the population of *Drosophila* during the treatment period comprises incubating the population of *Drosophila*, within a second temperature greater than the first temperature range for a first duration; and
wherein harvesting the population of *Drosophila* in response to the first concentration of the first target compound within the population of *Drosophila* exceeding the threshold concentration comprises harvesting the population of *Drosophila* in response to the first concentration of the first target compound within the population of *Drosophila* exceeding the threshold concentration.

9. The method of claim 7:
wherein applying the first dosage of the first stressor to the population of *Drosophila* to trigger production of the first target compound comprises applying the first dosage of the first stressor to the population of *Drosophila* to trigger production of the first target compound at a first rate; and
wherein applying a second dosage of the first stressor to the population of *Drosophila* during the second treatment cycle comprises applying the second dosage of the first stressor, the second dosage greater than the first dosage, to the population of *Drosophila* to trigger production of the first target compound at a second rate greater than the first rate.

10. A method comprising:
during an initial period, genetically modifying a population of *Drosophila* to produce a first target compound responsive to exposure to a first stressor comprising a heat stressor, the population of *Drosophila* comprising a genome comprising:
a first target sequence corresponding to the first target compound; and
a first promoter sequence linked to the first target sequence and associated with a first stressor;
during a growth period succeeding the initial period, cultivating the population of *Drosophila* for a first duration under a first set of growth conditions; and
during a treatment period succeeding the growth period:
during a first treatment cycle within the treatment period, applying a first dosage of the first stressor to the population of *Drosophila* to trigger production of the first target compound at a first rate proportional to the first dosage;
during a second treatment cycle succeeding the first treatment cycle within the treatment period, applying a second dosage of the first stressor, the second dosage greater than the first dosage, to the population of *Drosophila* to trigger production of the first target compound at a second rate greater than the first rate and proportional to the second dosage and
in response to a first concentration of the first target compound exceeding a threshold concentration during the treatment period, harvesting the population of *Drosophila*; and
during a purification period succeeding the treatment period:
homogenizing the population of *Drosophila* to form a blend comprising the first concentration of the first target compound; and
extracting the first target compound from the blend.

11. The method of claim 10, further comprising, during the treatment period:
removing the first stressor from the population of *Drosophila* and returning the population of *Drosophila* to the set of growth conditions during a first rest cycle succeeding the first treatment cycle and preceding the second treatment cycle; and
in response to the concentration of the first target compound falling below the threshold concentration after the second treatment cycle:
removing the first stressor from the population of *Drosophila* and returning the population of *Drosophila* to the set of growth conditions during a second rest cycle succeeding the second treatment cycle; and
applying a third dosage of the first stressor, greater than the second dosage, to the population of *Drosophila* to trigger production of the first target compound at a third rate, greater than the second rate, over a third treatment cycle succeeding the second rest cycle.

12. The method of claim 10:
wherein homogenizing the population of *Drosophila* to form the blend comprises mechanically homogenizing the population of *Drosophila* to form the blend comprising the first concentration of the first target compound and a second concentration of secondary components; and
wherein extracting the first target compound from the blend comprises:
  centrifuging the blend to form a supernatant comprising the first concentration of the first target compound and the second concentration of secondary components; and
  separating the first target compound from the secondary components of the supernatant via ion exchange chromatography.

13. The method of claim 1:
wherein applying the first dosage of the first stressor to the population of *Drosophila* during the treatment period comprises, during a first treatment cycle within the treatment period, applying the first dosage of the first stressor to the population of *Drosophila* to trigger production of the first target compound at a first rate proportional to the first dosage; and
wherein applying the second dosage of the first stressor to the population of *Drosophila* comprises, during the treatment period, during a second treatment cycle succeeding the first treatment cycle within the treatment period, applying the second dosage of the first stressor, the second dosage greater than the first dosage, to the population of *Drosophila* to trigger production of the first target compound at a second rate greater than the first rate and proportional to the second dosage.

14. The method of claim 10, wherein harvesting the population of *Drosophila* in response to the first concentration of the first target compound exceeding the threshold concentration comprises harvesting the population of *Drosophila* in response to the first concentration of the first target compound exceeding the threshold concentration of two percent.

15. The method of claim 10, wherein harvesting the population of *Drosophila* in response to the first concentration of the first target compound exceeding the threshold concentration comprises harvesting the population of *Drosophila* in response to the first concentration of the first target compound exceeding the threshold concentration of five percent.

16. The method of claim 10:
wherein genetically modifying the population of *Drosophila* to produce the first target compound responsive to exposure to the first stressor, the population of *Drosophila* comprising the genome comprising the first target sequence and the first promoter sequence linked to the first target sequence, further comprises genetically modifying the population of *Drosophila* to produce the first target compound and a second target compound responsive to exposure to the first stressor, the population of *Drosophila* comprising the genome comprising:
  the first target sequence corresponding to the first target compound;
  a second target sequence corresponding to the second target compound; and
  the first promoter sequence linked to the first target sequence and the second target sequence and associated with the first stressor;
wherein applying the first dosage of the first stressor to the population of *Drosophila* to trigger production of the first target compound comprises applying the first dosage of the first stressor to the population of *Drosophila* to trigger production of the first target compound and the second target compound;
wherein applying the second dosage of the first stressor to the population of *Drosophila* to trigger production of the first target compound comprises applying the second dosage of the first stressor to the population of *Drosophila* to trigger production of the first target compound and the second target compound;
wherein harvesting the population of *Drosophila* in response to the first concentration of the first target compound exceeding the threshold concentration comprises harvesting the population of *Drosophila* in response to the first concentration of the first target compound exceeding the threshold concentration and in response to a second concentration of the second target compound exceeding the threshold concentration;
wherein homogenizing the population of *Drosophila* to form the blend comprising the first concentration of the first target compound comprises homogenizing the population of *Drosophila* to form the blend comprising the first concentration of the first target compound and the second concentration of the second target compound; and
wherein extracting the first target compound from the blend comprises extracting the first target compound and the second target compound from the blend.

* * * * *